United States Patent
Durel-Crain

(12) 
(10) Patent No.: US 6,312,419 B1
(45) Date of Patent: Nov. 6, 2001

(54) TAMPON STRING TAB AND METHOD FOR ATTACHMENT

(76) Inventor: Maxie A. Durel-Crain, 301 Renee Ave., Lafayette, LA (US) 70503

( * ) Notice: Subject to any disclaimer, the term of this patent is extended or adjusted under 35 U.S.C. 154(b) by 0 days.

(21) Appl. No.: 09/285,616

(22) Filed: Apr. 3, 1999

(51) Int. Cl.$^7$ .................................................. A61F 13/15
(52) U.S. Cl. ...................................... 604/385.18; 604/904
(58) Field of Search ................................. 604/904, 363, 604/14, 15, 385.17, 385.18

(56) References Cited

U.S. PATENT DOCUMENTS

| | | | |
|---|---|---|---|
| 1,555,708 | * | 9/1925 | Gale ....................................... 604/904 |
| 3,037,506 | * | 6/1962 | Penksa .................................. 604/904 |
| 3,948,257 | * | 4/1976 | Bossak .................................. 604/904 |
| 4,277,902 | * | 7/1981 | Miniaci et al. ............................ 40/2 |
| 4,332,251 | * | 6/1982 | Thompson ........................... 604/904 |
| 4,341,214 | | 7/1982 | Fries et al. . |
| 4,950,280 | * | 8/1990 | Brennan ............................... 604/904 |
| 5,338,586 | * | 8/1994 | Chalfin ................................... 428/28 |
| 5,383,891 | * | 1/1995 | Walker .................................. 604/904 |
| 5,458,589 | | 10/1995 | Comin-DuMong . |
| 5,533,990 | * | 7/1996 | Yeo ....................................... 604/363 |
| 5,566,435 | | 10/1996 | Brown, Jr. . |
| 5,659,934 | | 8/1997 | Jessup et al. . |
| 5,674,239 | * | 10/1997 | Zadini et al. ......................... 604/904 |
| 5,755,706 | * | 5/1998 | Kronenthal et al. ................. 604/904 |
| 5,807,372 | | 9/1998 | Balzar . |
| 5,840,055 | * | 11/1998 | Sgro ....................................... 604/11 |
| 5,964,636 | * | 10/1999 | Carrera ................................. 446/220 |

\* cited by examiner

*Primary Examiner*—Dennis Ruhl
(74) *Attorney, Agent, or Firm*—Garvey, Smith, Nehrbass & Doody, L.L.C.

(57) ABSTRACT

An accessory in the form of a tab, tassel or puff ball attached to a tampon string to facilitate the tactile location and manipulation of the tampon string during urination. The accessory may also help prevent the tampon string from being retracted into the vagina. Additional embodiments are illustrated along with a method for extending the tampon string with the accessory attachment having the capability of being adhered to the user's body or undergarment.

10 Claims, 2 Drawing Sheets

TAMPON STRING TAB AND METHOD FOR ATTACHMENT

BACKGROUND OF THE INVENTION

1. Field of the Invention

This invention relates generally to feminine hygienic tampons having strings attached thereto for withdrawal. More particularly, the invention relates to a method for attaching an accessory or tab to the string to facilitate locating and preventing dislocation of the tampon string.

2. General Background

The tampon industry estimates that on average a women will use 11,400 tampons in her lifetime. Many of these tampon users are young, highly active women who become so accustomed to the presence of the tampon that they literally forget it is in place. Tampons are generally provided with a string which extends outside the vagina to assist in removal of the tampon from the body cavity. This string generally comprises a string looped around a portion of the tampon in a manner which produces a pair of string ends knotted together at their free end. Therefore, due to frictional migration and the expansion and contraction of the vagina, especially during physical activity, the tampon can get lodged near the back of the vagina or rotated in such a manner that the string is withdrawn into the vagina cavity. Since the string is not easily visible and not capable of being felt, women often forget to change the tampon every 4–6 hours as recommended by the manufacturer. On occasion some women forget and accidentally insert a new tampon without removing the previous one. Such action leads to serious complication. Some women who are not familiar with their bodies sometimes panic, fearing that the tampon is lost and that perhaps surgery will be required to retrieve the tampon. It is estimated that each gynecologist experiences the need to retrieve lost tampons an average of twice per month. Therefore, this is serious problem affecting thousands of women nationally every year. Tampons which are not removed regularly provide a breeding ground for staphylococcus Aureus, a bacterium which leads to a number of serious medical problems, such as toxic shock syndrome.

The tampon string is also a problem during urination. Most women, assuming they remember the tampon string at all, have a preference as to the question of whether to try and locate the short string or simply urinate on it thus leaving the string wet and subject to bacterial infection. Most tampon manufacturers provide a relatively short, string usually less than three inches, making the movement of the string to a position out of the way during urination an awkward maneuver at best, thus it is simply easier to wet the string. Since most tampon strings are made of cotton, they absorb moisture readily and thus further provide a breeding ground for infectious bacteria. To make matters worse, women seldom wash their hands in public rest rooms. This phobia makes them reluctant to search for and handle the short, often moist, tampon string.

It is therefore evident that the above problems need to be addressed in a manner which will allow women to retrieve a tampon more readily and become more aware of its presence.

SUMMARY OF THE INVENTION

The present invention provides an accessory in the form of a tab, tassel or puff ball attached to a tampon string. The accessory is intended to help the tampon user more easily locate and manipulate the tampon string during urination and may be more readily discerned if the string is being retracted into the vagina. Subsequent illustrations provide a method for extending the length of the tampon string with the accessory attachment and further having the optional capability of being adhered to the users body or undergarment.

The intended purpose of the accessory is to help draw attention to the tampon and facilitate the location and manipulation of the tampon string during urination. The accessory further draws the user's attention to the presence of the tampon and, therefore, serves as a reminder to change the tampon frequently. The accessory also helps to prevent migration of the tampon string into the vagina.

BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein.

DETAILED DESCRIPTION OF THE PREFERRED EMBODIMENT

Figure 1:
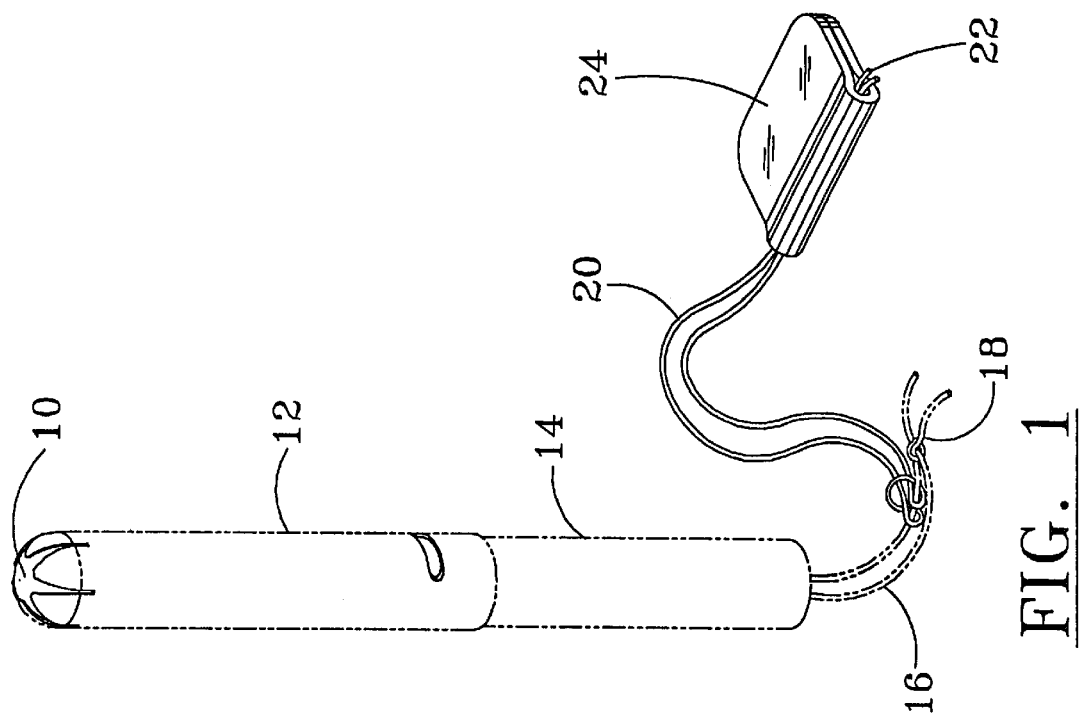
FIG. 1 is an isometric view of a tampon and insertion tube and a first embodiment of the invention.

As illustrated in FIG. 1, tampons 10 are often supplied installed within an insertion tube 12 having a plunger portion 14. The tampon string attached to the tampon 10 extends longitudinally through the hollow tubular plunger 14 the string 16 generally comprising the two ends of the same string knotted at their free end 18. The string 16 usually is not more than three inches in length. It is anticipated that since vast numbers of these tampons are already available, an attachment needs to be provided in the form of an extension string loop 20 which can be threadably looped through the existring string 16 behind the knot at the free end 18 in a manner whereby the two strings are connected, thus increasing the string to between 3 and 6 inches long. The extension string 20 loop is connected at its free end 22 to a tab 24 which is adhered or otherwise secured around a portion of the extension string 20. The tab 24 can be of any configuration, but preferably one which is not excessively bulky or irritating such as a length of cloth backed tape folded in half or otherwise secured around the string. However, the tab should be sufficiently large to prevent retraction into the vagina as a result of frictional migration or other exertion. The extension string 20 extends the length of the string 16, usually adding about 6 to 7 inches in the overall length for an overall length of about 11 inches, and results in an extended string 20 and a tab 24 which allows the user to more easily locate and position the string during urination.

Figure 2:
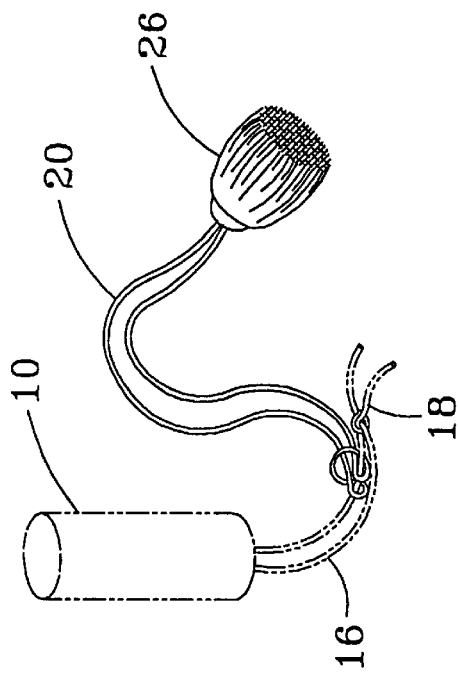
FIG. 2 is an isometric view of a tampon shown in phantom connected to a second embodiment of the invention.

As seen in FIG. 2, the string accessory may be a tassel 26 or the like having several strands of thread which could be used at the end of the extension string 20. This embodiment provides a tactilely noticable body at the end of the string 20, yet the accessory will lie virtually flat and invisible under the user's garments.

Figure 3:
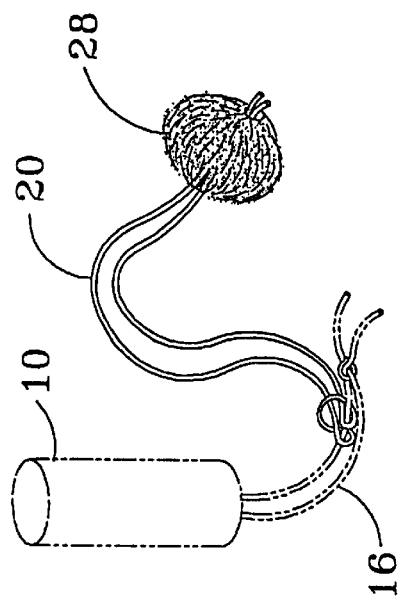
FIG. 3 is an isometric view of a tampon shown in phantom connected to another embodiment of the invention.
Figure 4:
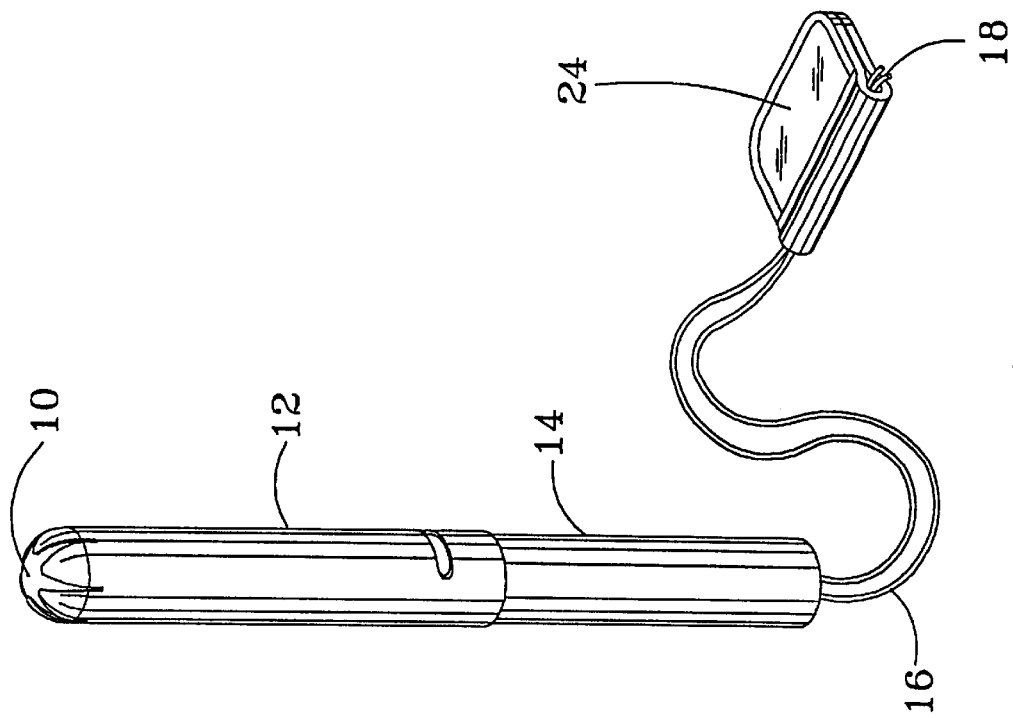
FIG. 4 is an isometric view of a tampon and insertion tube and yet another embodiment of the invention.

The accessory seen in FIG. 3 may also be a non-absorbent puff ball, such as a knit globe or spherical body 28 having a hollow core which folds along its equator, or other such soft, non-absorbent body which will tend to expand and collapse diametrically upon axial compression along its polar axis The tampon string 16 as illustrated in FIG. 4 can certainly be extended during manufacture, thus avoiding the need to provide an extension string 20 The tab 24 may also be attached during manufacture or provided as an optional accessory item in the form of a peel off tab which may be folded in half around the knotted end 18 of the string 16 as shown, the sticky, peel-off sides folded to face each other and being adhered to the string 16.

Figure 6:
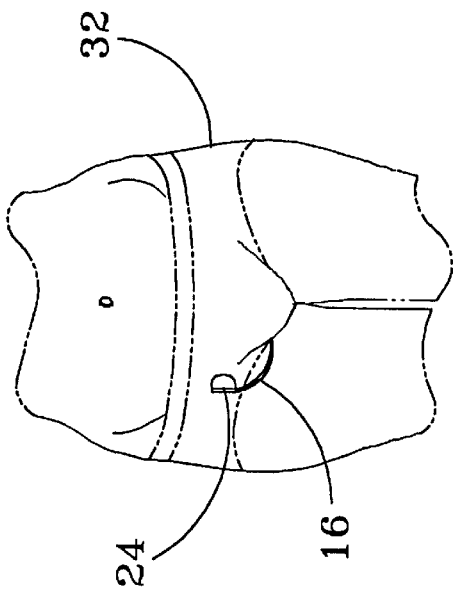
FIG. 6 is a partial isometric view of a woman, illustrating the invention in use.
Figure 5:
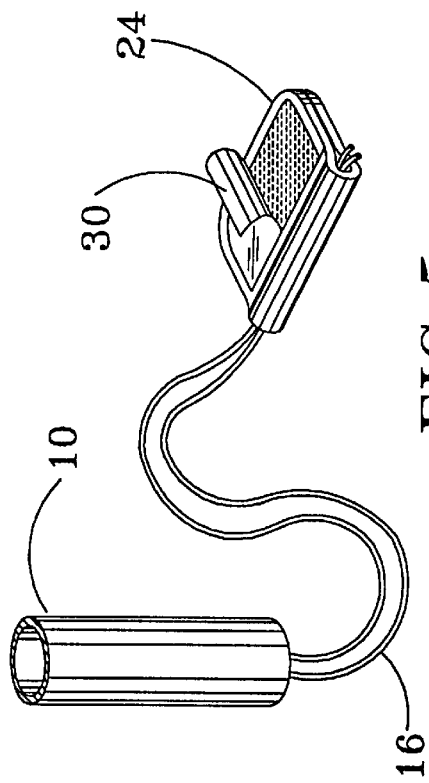
FIG. 5 is an isometric view of a tampon with the invention attached.

It is also anticipated that the tab 24 may be a double sided, soft cloth tape having a peel-off backing 30 as seen in FIG. 5 which, when removed, provides a sticky surface which allows the tab 24 to be temporarily and removably adhered to a portion of the user's body or undergarment. Preferably the tab 24 would be adhered to the user's body as seen in FIG. 6 in the vicinity of the upper thigh normally covered by the user's under garments.32.

In use, the accessories 24,26,28 should be sufficiently large to attract the user's attention any time the lower under garment is removed, thus reminding the user to change the tampon frequently. The string should be sufficiently long to allow the tampon user to readily locate the string 16, 20 without searching and hold or position it to prevent saturation during urination. The accessories 24,26,28 should also be sufficiently large to prevent migration into the vagina, yet light and resilient enough to be virtually invisible when under the user's clothing.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

What is claimed is:

1. A method for enhancing a tampon user's ability to locate and manipulate a tampon string during urination and aid in the prevention of tampon string retraction into said user's vagina comprising the steps of providing an accessory attachable to the free end of the tampon string, further comprising the step of providing an extension string with said accessory attached and securing said extension string to said tampon string.

2. The method according to claim 1 wherein said accessory is a piece of tape ½ to 2 inches long and ½ to 2 inches wide secured to said extension string, the tape having a sticky surface.

3. The method according claim 1 wherein said accessory is a piece of hypo-allergenic tape ½ to 2 inches wide and ½ to 2 inches long secured to said extension string.

4. The method according to claim 1 wherein said accessory is a piece of tape which can be rolled into a cylindrical shape and unrolled to allow the use of portions of tape.

5. Apparatus including a tampon having a tampon string having an end and a tab comprising a length of tape secured around the end of the tampon string, the tape having a sticky surface.

6. The apparatus according to claim 5 wherein said tab further comprises a peel-off backing which, when removed, exposes the sticky surface.

7. The apparatus according to claim 5 wherein said tab is a piece of tape ½ to 2 inches long and ½ to 2 inches wide secured to the string.

8. The apparatus according claim 5 wherein said tab is a piece of hypo-allergenic tape ½ to 2 inches wide and ½ to 2 inches long secured to the string.

9. The apparatus according to claim 5 wherein said tab is a piece of tape which can be rolled into a cylindrical shape and unrolled to allow the use of portions of tape.

10. A method for enhancing a tampon user's ability to locate and manipulate a tampon string during urination and aid in the prevention of tampon string retraction into said user's vagina comprising the steps of:

providing an accessory attachable to the free end of the tampon string, extending the length of a tampon string to between 3 and 11 inches long and attaching said accessory, and adhering said accessory to a portion of said user's body.

* * * * *